United States Patent
Huang (10) Patent No.: US 8,496,801 B2
(45) Date of Patent: Jul. 30, 2013

(54) METHOD AND SYSTEM FOR CHECKING AN ELECTROMECHANICAL BIOSENSOR

(75) Inventor: Dijia Huang, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 799 days.

(21) Appl. No.: 11/988,426

(22) PCT Filed: Jul. 24, 2006

(86) PCT No.: PCT/US2006/028918
§ 371 (c)(1),
(2), (4) Date: Jan. 7, 2008

(87) PCT Pub. No.: WO2007/014231
PCT Pub. Date: Feb. 1, 2007

(65) Prior Publication Data
US 2009/0127135 A1    May 21, 2009

Related U.S. Application Data

(60) Provisional application No. 60/702,670, filed on Jul. 26, 2005.

(51) Int. Cl.
*G01N 27/327* (2006.01)
*G01N 27/416* (2006.01)

(52) U.S. Cl.
USPC ....... 205/792; 204/403.01; 204/406; 205/779

(58) Field of Classification Search
USPC .............. 204/400–435; 205/775–794.5; 73/53.01–64.56; 435/4–40.52, 287.1–288.7; 436/62–71, 500–548
See application file for complete search history.

(56) References Cited

U.S. PATENT DOCUMENTS 5,352,351 A    10/1994 White et al. .................. 204/406
5,503,036 A    4/1996 Nguyen et al. ............. 73/864.34

(Continued)

FOREIGN PATENT DOCUMENTS

EP    1 116 953 A2    7/2001
EP    1 256 798 A1    11/2002

(Continued)

OTHER PUBLICATIONS

Written Opinion corresponding to International Patent Application No. PCT/US2006/028918, European Patent Office, dated Nov. 13, 2006, 6 pages.

(Continued)

*Primary Examiner* — Keith Hendricks
*Assistant Examiner* — Susan D Leong
(74) *Attorney, Agent, or Firm* — Nixon Peabody LLP (57) ABSTRACT

A method of operating a meter for determining the concentration of an analyte in a current sample and for self-detecting electrical connection errors like short or open circuit between the electrodes of a biosensor. The method includes providing a connector with a plurality of contacts and coupling each of the plurality of contacts to one of a plurality of electrical leads on a biosensor, such that each of the plurality of connector contacts electrically contacts a corresponding one of the plurality of electrical leads. The meter obtains a first measurement between a pair of the plurality of connector contacts prior to the fluid sample being applied. The meter also obtains a second measurement between the pair of the plurality of connector contacts after the fluid sample is applied. In response to either the first or the second measurements being outside a predetermined range, a fault is indicated.

20 Claims, 8 Drawing Sheets

U.S. PATENT DOCUMENTS

| | | | |
|---|---|---|---|
| 5,665,215 A | 9/1997 | Bussmann et al. | 204/403 |
| 5,777,221 A | 7/1998 | Murthy et al. | 73/149 |
| 6,370,942 B1 | 4/2002 | Dunfee et al. | 73/37 |
| 6,707,544 B1 | 3/2004 | Hunter et al. | 356/237.5 |
| 6,841,052 B2 | 1/2005 | Musho et al. | 204/401 |
| 2002/0150351 A1* | 10/2002 | Nakura et al. | 385/75 |
| 2003/0050546 A1* | 3/2003 | Desai et al. | 600/347 |
| 2003/0113227 A1 | 6/2003 | Eyster et al. | 422/56 |
| 2003/0159945 A1* | 8/2003 | Miyazaki et al. | 205/777.5 |
| 2003/0187338 A1* | 10/2003 | Say et al. | 600/345 |
| 2004/0024495 A1* | 2/2004 | Sunderland | 700/299 |
| 2004/0222092 A1 | 11/2004 | Musho et al. | 204/401 |
| 2004/0265855 A1 | 12/2004 | Pessara et al. | 435/6 |
| 2006/0231424 A1* | 10/2006 | Harding et al. | 205/792 |

FOREIGN PATENT DOCUMENTS

| | | |
|---|---|---|
| EP | 1 447 452 A1 | 8/2004 |
| EP | 1 452 854 A1 | 9/2004 |
| WO | WO 03/058191 A2 | 7/2003 |
| WO | WO 03/091717 A1 | 11/2003 |
| WO | WO 2004/029605 A1 | 4/2004 |

OTHER PUBLICATIONS

International Search Report corresponding to International Patent Application No. PCT/US2006/028918, European Patent Office, dated Nov. 13, 2006, 5 pages.

\* cited by examiner

METHOD AND SYSTEM FOR CHECKING AN ELECTROMECHANICAL BIOSENSOR

CROSS-REFERENCE TO RELATED APPLICATIONS

This application claims priority to Application No. 60/702,670 filed on Jul. 26, 2005, which is incorporated by reference in its entirety.

FIELD OF THE INVENTION

The present invention relates generally to an electrochemical biosensor and, more particularly, to a new and improved biosensor meter and method for self-detecting electrical connection errors between a biosensor and the meter, which is used in analyzing at least one analyte in a fluid contained therein (e.g., blood glucose, cholesterol).

BACKGROUND OF THE INVENTION

People suffering from various forms of diabetes routinely need to test their blood to determine the level of blood glucose. The results of such tests can be used to determine what, if any, insulin or other medication needs to be administered. In one type of blood glucose testing system, biosensors are used to test a sample of blood.

Such a biosensor may have a generally flat, rectangular shape with a front or testing end and a rear or terminal end. The biosensor contains multiple electrodes near its testing end, each of which electrically links to a corresponding lead at a terminal end of the biosensor. On the electrodes, there is at least one layer of reagent consisting of enzyme, mediator and certain inactive ingredients. The reagent will enzymatically react with blood glucose and produce redox current at the electrodes. The testing end of the biosensor is adapted to receive the fluid being tested, for example, blood that has accumulated on a person's finger after the finger has been pricked. The fluid is drawn into a capillary channel that extends in the biosensor from the tip of the testing end to the reagent/electrodes by capillary action so that a sufficient amount of fluid to be tested is drawn into the biosensor. The fluid then reacts with the reagent in the biosensor with the result that an electrical signal indicative of the blood glucose level in the blood being tested is supplied from the electrodes to their corresponding leads located at the rear or terminal end of the biosensor.

In such biosensors, multiple electrodes, and hence, multiple leads are used. When a biosensor is inserted into its associated meter and is positioned into the testing position, such leads are connected to the meter electronic circuitry via a connector in the meter. If the biosensor is already in the meter, then it is positioned in the testing position. The connector, in general, has the same number of contacts as the leads on the biosensor (although in some applications, there can be more contacts or more leads). Each lead is connected to an individual connector contact, which in turn is connected to the meter circuitry. However, connection errors, such as a short or open, could occur. A short condition occurs, if, not by design, two connector contacts touch the same lead or one of the contacts touches more than one lead. An open condition occurs if, not by design, a contact does not touch any lead. Such short and open conditions could cause an erroneous reading, which could result in harmful consequences. Such faulty meter-sensor connections may be caused by damaged contacts in the connector or defective leads on the biosensor. Therefore, it is crucial for such a meter to self-detect the meter-sensor connection errors such as a short condition or an open condition.

SUMMARY OF THE INVENTION

According to one embodiment of the present invention, a method and system for determining short and open conditions between the meter and the biosensor is provided.

According to one embodiment of the present invention, a method of operating a meter for determining the concentration of an analyte in a fluid sample is provided. The method includes providing a connector with a plurality of contacts and coupling each of the plurality of contacts to one of a plurality of electrical leads on a biosensor, such that each of the plurality of connector contacts electrically contacts a corresponding one of the plurality of electrical leads. The meter obtains a measurement between at least one pair of the plurality of connector contacts that connect to a pair of adjacent leads prior to the fluid sample being applied. In some embodiments, it is preferred to obtain a measurement between every pair of the connector contacts which connect to a unique pair of adjacent leads prior to the fluid sample being obtained. The meter also obtains a measurement between the at least one pair of the plurality of connector contacts after the fluid sample is applied. In some embodiments, it is preferred to obtain the measurement between a common connector contact and every other connector contact after the fluid sample is applied.

According to another embodiment of the present invention, a method of operating a meter for determining the concentration of an analyte in a fluid sample is provided. The method includes inserting a biosensor into the meter and into the testing position. If the biosensor is already in the meter, then the biosensor is positioned in the testing. The biosensor includes a plurality of leads; by design, the plurality of leads each contact one of a plurality of connector contacts in the meter. A current measurement is obtained via the meter. The current measurement is obtained between at least one pair of the of the plurality of connector contacts in the meter, which connect to a pair of adjacent leads. In some embodiments, it is preferred that the meter obtains a measurement between every pair of the connector contacts that connect to a unique pair of adjacent leads. However, this is not required. A fluid sample is introduced into the meter. The meter then obtains a current measurement after the fluid sample is applied between at least one pair of connector contacts. In some embodiments, it is preferred that the meter obtains a measurement between a common connector contact and every other connector contact after the fluid sample is obtained. However, this is not required.

According to yet another embodiment of the present invention, a test system for determining the concentration of an analyte in a fluid sample is provided. The system includes a meter having a connector with a plurality of contacts and a biosensor having a plurality of leads. By design, each of the plurality of leads contacts a respective one of the plurality of contacts. The meter takes a measurement between at least one pair of the plurality of connector contacts both prior to the fluid sample being applied and after the fluid sample is applied. In some embodiments, it is preferred that the meter obtains a measurement between every pair of the connector contacts that connect to a unique pair of adjacent leads. Also, in some embodiments, it is preferred that the meter obtains a measurement between a common connector contact and every other connector contact after the fluid sample is obtained. However, these additional measurements between additional pairs of contacts are not required.

The above summary of the present invention is not intended to represent each embodiment, or every aspect, of the present invention. Additional features and benefits of the present invention are apparent from the detailed description and figures set forth below.

DESCRIPTION OF ILLUSTRATED EMBODIMENTS

The present invention is directed to a system including a biosensor and its associated meter. As will be described below in more detail, the present invention relates to system and method of detecting electrical shorts and openings in connection between a biosensor and its meter.

To best understand the invention, a brief discussion regarding biosensors and meters will follow. The invention is directed to a multi-contact connector assembly to be used in a multi-tests meter that contains a plurality of biosensors. The biosensors are used to determine concentrations of at least one analyte in a fluid. Analytes that may be determined using a biosensor connecting the meter via multi-contact connector assembly include glucose, lipid profiles (e.g., cholesterol, triglycerides, LDL and HDL), microalbumin, hemoglobin $A_{1C}$, fructose, lactate, or bilirubin. The present invention is not limited, however, to determining these specific analytes and it is contemplated that other analyte concentrations may be determined. The analytes may be in, for example, a whole blood sample, a blood serum sample, a blood plasma sample, or other body fluids like ISF (interstitial fluid) and urine.

Figure 1:
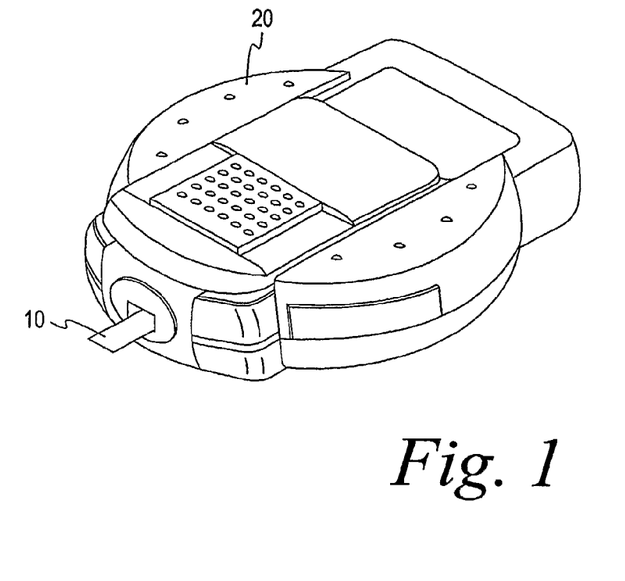
FIG. 1 is a perspective view of a meter according to one embodiment of the present invention.

The plurality of biosensors is typically stored in a disposable cartridge. For example, the plurality of biosensors may be stored in a sensor pack where the biosensors are individually packaged in sensor cavities (e.g., a blister-type pack). An example of biosensor cartridge mounted inside a meter 20 is depicted in FIG. 1. As shown, a single biosensor 10 has been ejected from the cartridge for use. The disposable cartridge may be a blister-type pack, which includes a plurality of biosensors 10. The disposable cartridge may include biosensors 10 in a stacked design, which is also known in the art. Other types of cartridges may also be used. In the blister-type pack, each biosensor 10 is individually stored in a respective one of sensor cavities. It is contemplated that other sensor packs that individually hold the biosensors may be used. The disposable cartridge is further described at U.S. Publication No. 2003/0032190 that published on Feb. 13, 2003 and is entitled "Mechanical Mechanism for a Blood Glucose Sensor-Dispensing Instrument."

The biosensors 10 to be used in the cartridges are typically provided with a capillary channel that extends from the front or testing end of the biosensors to electrodes and reagent material disposed in the electrodes. When the testing end of the biosensor is placed into fluid (e.g., blood that is accumulated on a person's finger after the finger has been pricked), a portion of the fluid is drawn into the capillary channel by capillary action. The analyte in the fluid then enzymatically reacts with the reagent in the biosensor so that current is generated at the electrodes of the biosensor. Such electrical current is indicative of the analyte (e.g., glucose) level in the fluid being tested and subsequently transmitted to an electrical assembly of the meter 20.

Reagent material that may be used to determine the glucose concentration include analyte specific enzyme (e.g., glucose oxidase) and mediator (e.g., potassium ferricyanide). It is contemplated that other reagent material may be used to determine the glucose concentration such as glucose dehydrogenase pyrrolo-quinoline quinone glucose dehydrogenase and potassium ferricyanide. The selected reagent may influence items such as the stability of the reagent and the length of time needed to perform the testing to determine the analyte concentration.

Figure 2:
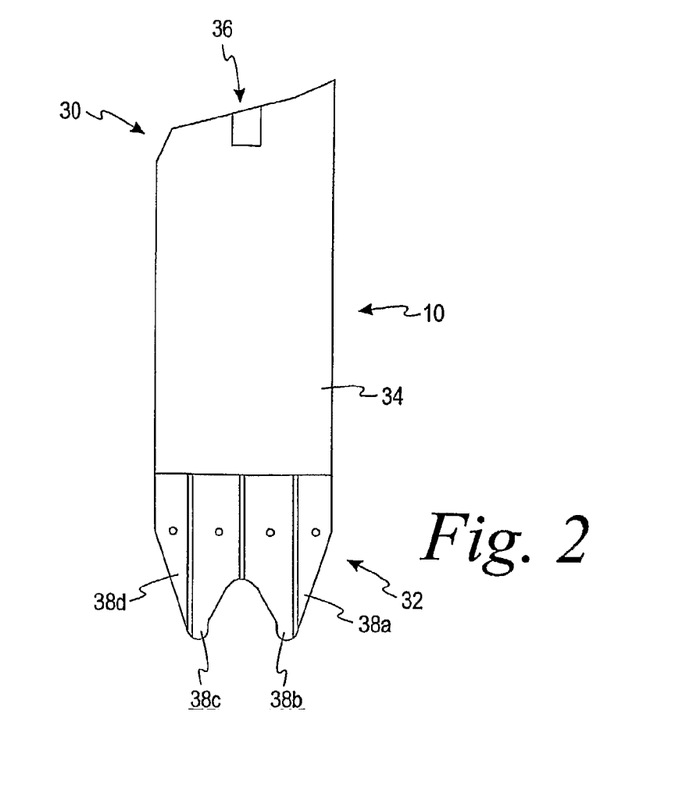
FIG. 2 is a top view of a biosensor according to one embodiment of the present invention.

One non-limiting example of a biosensor is shown in FIG. 2. FIG. 2 depicts the biosensor 10 that includes a biosensor test end 30 and a biosensor terminal end 32. The biosensor test end includes a lid 34 and a capillary channel 36. A plurality of electrodes, such as a working electrode, a counter electrode, and some error detection electrodes are located inside the capillary channel 36. These electrodes are each electrically connected a lead 38a, 38b, 38c, 38d. Although not shown, the biosensor 10 includes a fluid-receiving area that contains reagent. The operation of fluid-receiving area with reagent and the electrodes on the biosensors is known to those skilled in the art and will therefore not be described in further detail. Examples of electrochemical biosensors, including their operation, may be found at, for example, U.S. Patent Application published as 2001/0042683 and EP 1152239. It is contemplated that other electrochemical biosensors may be employed.

Figure 3:
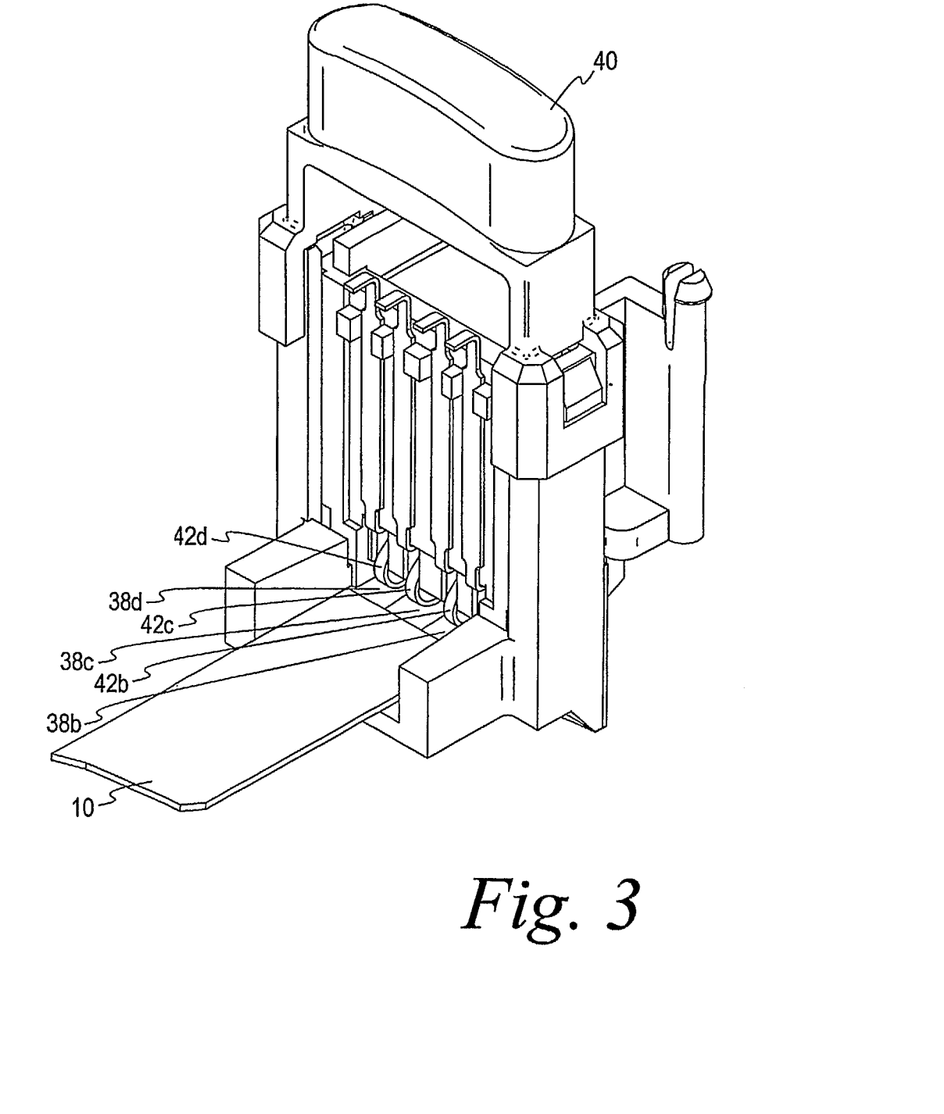
FIG. 3 is a perspective view of the component parts of a biosensor connector and a sensor of the meter of FIG. 1.
Figure 4A:
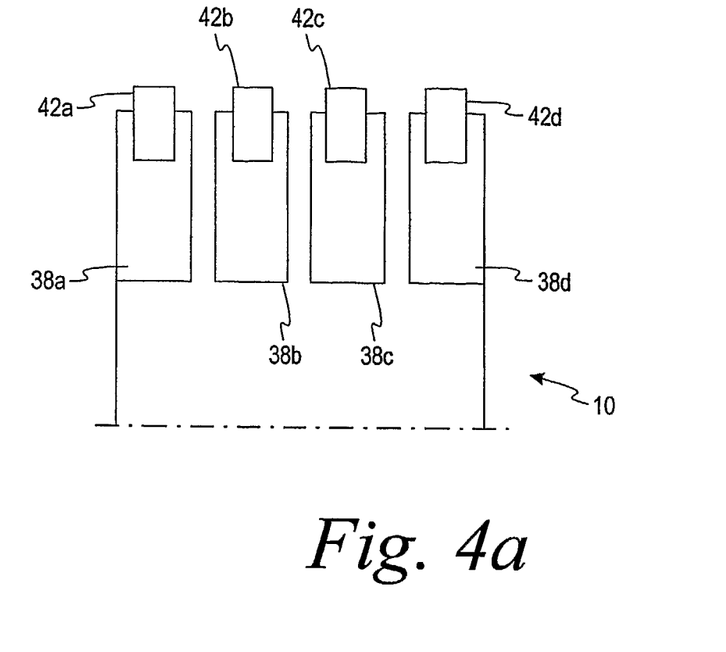
FIG. 4a is a schematic of the proper connection between leads and connector contacts of the test device of FIG. 1.
Figure 4B:
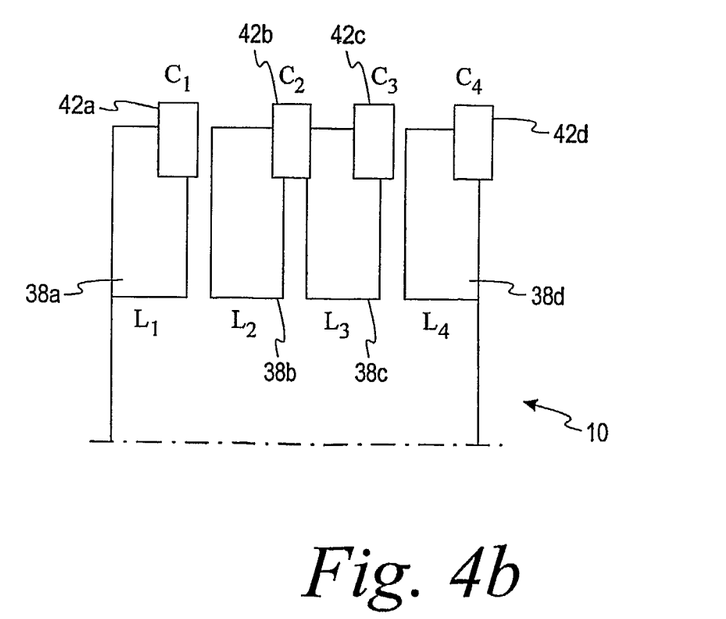
FIG. 4b is a schematic of the leads and connector contacts in a short condition.

Referring now to FIG. 3, a multi-contact connector assembly 40 according to one embodiment is shown. The multi-contact connector assembly 40 is adapted to make a connection between the biosensor 10 and the electronic system of the meter 20 (FIG. 1). The software located in the meter 20 uses the electrical signals to output at least one analyte concentration of the fluid (e.g., a blood glucose level). The multi-contact connector assembly 40 comprises a plurality of connector contacts 42a, 42b, 42c, 42d (shown in FIGS. 3, 4a-c, 5). The biosensor 10 is inserted into the multi-contact connector assembly 40 such that each of the plurality of connector contacts 42a, 42b, 42c, 42d connects to one of the corresponding leads 38a, 38b, 38c, 38d of the biosensor 10. As shown in FIGS. 3, 4a, 4b, each of the connector contacts 42a, 42b, 42c, 42d is fixed in the multi-contact connector assembly 40 and positioned to make contact with the biosensor 10.

In this embodiment, the multi-contact connector assembly 40 of FIG. 3 includes exactly four connector contacts 42a (shown in FIG. 5), 42b, 42c, 42d. It is contemplated that the multi-contact connector assembly may have any number of connector contacts, so long as the number of connector contacts corresponds to the number of leads on the biosensor 10.

Turning now to FIG. 4a, a schematic illustrating a proper connection between the four leads 38a, 38b, 38c, 38d of the biosensor 10 and the four connector contacts 42a, 42b, 42c, 42d is shown. As shown, each of the connector contacts 42a, 42b, 42c, 42d contacts one and only one of the leads 38a, 38b, 38c, 38d.

However, there may be instances in which one of the connector contacts 42a, 42b, 42c, 42d may contact two or more leads 38a, 38b, 38c, 38d due to either defective contacts in the connector or defective leads on the biosensor 10. In FIG. 4b, the connector 42b is contacting both lead 38b and lead 38c, creating a short condition. As stated above, a short condition may cause a meter malfunction. Such malfunction could result in an erroneous reading, which may cause user frustration or even bodily harm.

Figure 4C:
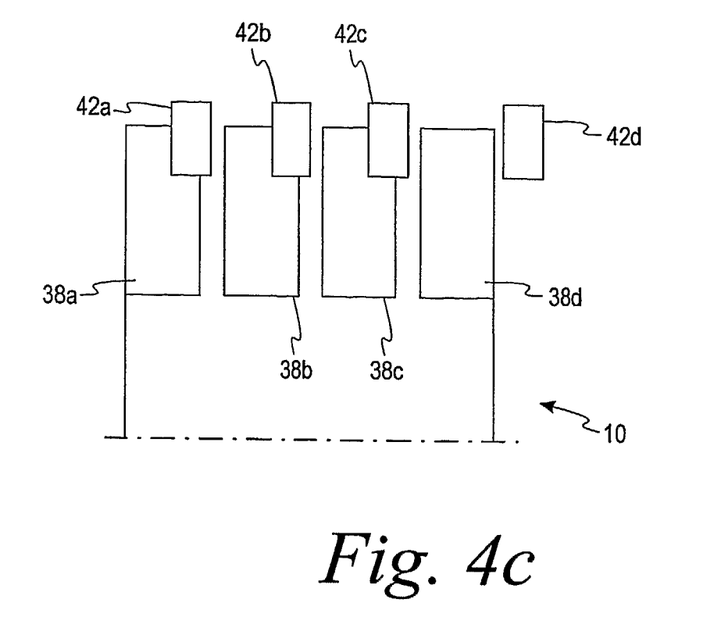
FIG. 4c is a schematic of the leads and connector contacts in an open condition.

Another potential problem is if there is an open condition. An open condition is shown in FIG. 4c in which the connector 42d is not contacting any leads, due to either defective contacts in the connector or defective leads on the biosensor. Like the case of a short condition, an open condition may also cause a meter malfunction. Such a malfunction could result in an erroneous reading, potentially causing user frustration or even bodily harm.

Figure 5:
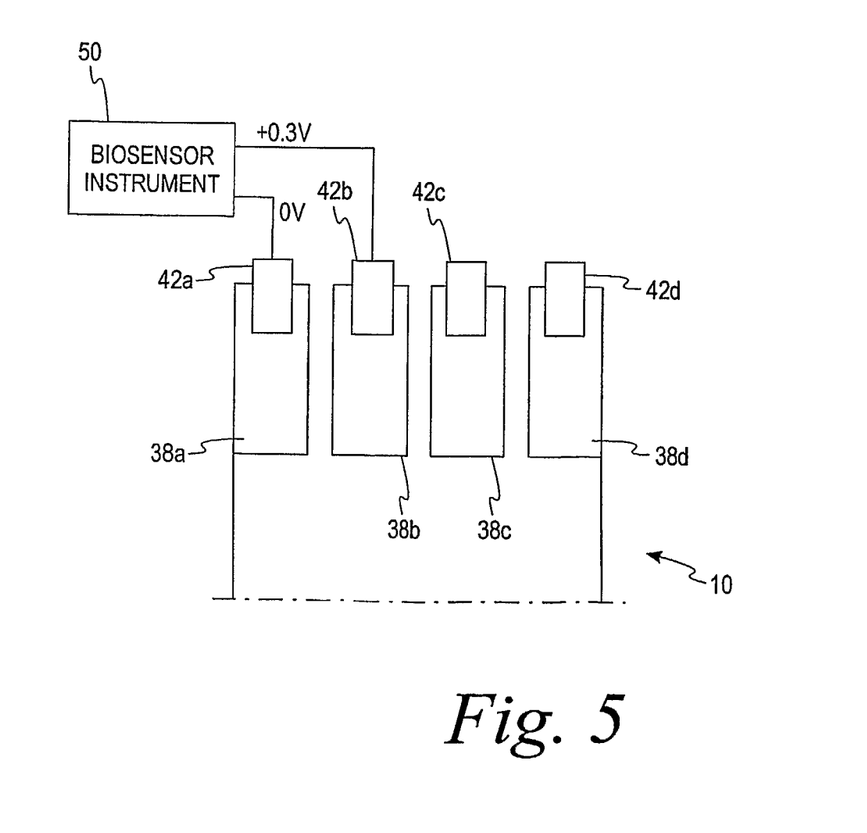
FIG. 5 is a schematic of the leads and connector contacts coupled to the circuitry of the test device according to one embodiment of the present invention.

Turning now to FIG. 5, a schematic for testing the meter/biosensor connection is illustrated. To determine whether an open condition or a short condition exists, the meter 20 applies a voltage (in one embodiment of about 0.3 volts) and then measures the current between each pair of neighboring connector contacts (shown measuring between connector contact 42a and connector contact 42b, but each pair is measured). Before the fluid sample is applied (i.e., a "dry" condition—meaning that the reagent on the biosensor 10 is dry), the current between the two connector contacts being measured (in the illustrated case, between connector contacts 42a and 42b) should be zero. If the meter 20 measures a current (or any current over a predetermined threshold, for example, about 30 nA), then a short condition exists between the two connector contacts 42a, 42b, and the user will be alerted to the faulty condition. Similarly, the meter will apply a voltage and measure the current between the connector contacts 42b and 42c, and between the connector contacts 42c and 42d. In other embodiments involving more (or less) connector contacts 42, the meter 20 desirably measures the current between each pair of adjacent connector contacts 42 or each pair of connector contacts 42 which connect to a pair of adjacent leads on the biosensor 10.

In some embodiments, the number of connector contacts in the meter may not equal the number of leads. In such applications, a lead on a sensor, by design, may contact more than one connector contact or a connector contact may touch more than one lead. In such a situation, there would be a "short" condition that exists. However, such a "short" is by design, and not by an error condition, and the meter 20 would not register it as a fault.

However, testing the current during a dry condition does not test whether an open condition exists. If one of the connector contacts 42 is not contacting a lead, the current during the dry condition from that connector contact would always be zero, which is the same as if there is no short condition between the connector contacts. To detect an open condition, the meter 20 also applies a voltage and then measures the current between each predefined pair of connector contacts (illustrated here as connector contacts 42a, 42b) after the fluid sample has been applied (a "wet" condition—meaning that the reagent of the biosensor 10 is wet), preferably after normal analyte measures are complete. During the wet condition, the leads are electrically coupled via the fluid sample, meaning that an electrical circuit is created. In some embodiments, the current measured should be greater than a predetermined threshold, for example, about 100 nA. During the wet condition, if the current is near zero, then an open condition exists and the user is alerted to the faulty condition. The same detection method will be applied to connector contacts 42a and 42c and to connector contacts 42a and 42d. In other embodiments involving more (or less) contacts 42, a current measurement is desirably measured between a common connector contact (e.g., connector contact 42g) and every other connector contact (e.g., connector contacts 42b, 42c, 42d). In essence, the connection error detection method utilizes the biosensor's different electrical characteristics under dry condition (before a fluid sample is applied) and wet condition (after the fluid sample is applied) to detect short and open conditions with a same type of current measurement.

Figure 6A:
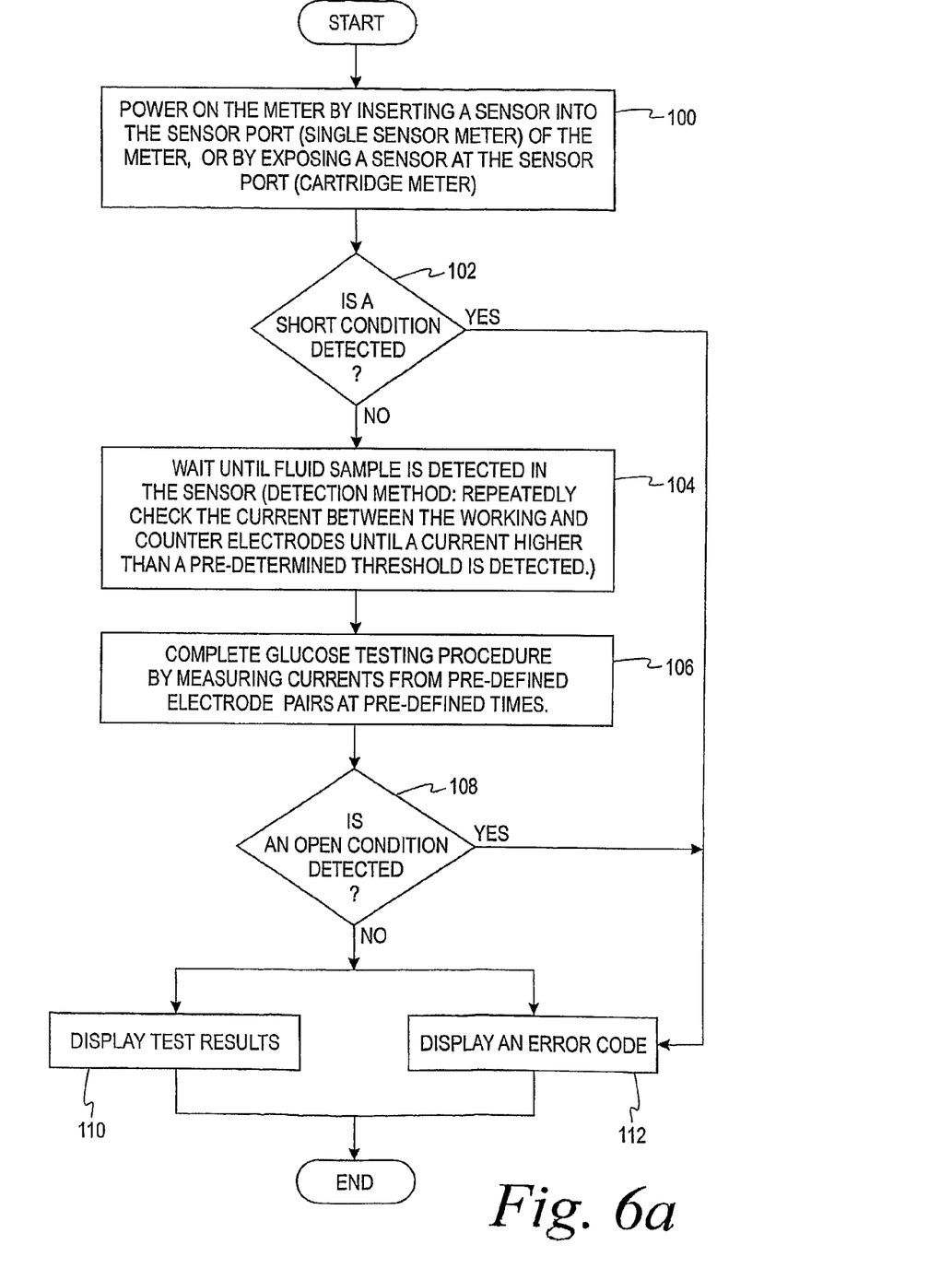
FIGS. 6a-6c are flowcharts describing the method of operation according to one embodiment of the present invention.

Turning now to FIG. 6a, a flow chart of the operation of the instrument 20 will be described according to one method. At step 100, the meter 20 will be powered on by either ejecting the biosensor 10 from the cartridge 10 (if a cartridge meter) into the sensor port of the meter 20 or bringing the biosensor 10 into the meter 20 (if a single sensor meter) and into the testing position. In either scenario, the biosensor is positioned into the testing position. The meter 20 then detects whether there is a "short" condition at step 102. This will be discussed further in connection to FIG. 6b, described below. If a "short" condition is detected, the process advances to step 112 and an error code is displayed.

If a short condition is not detected, the process continues to step 104, and the meter 20 then detects whether a fluid sample is detected in the biosensor 10. The process continues to repeat step 104 until a fluid sample is detected. The presence of a fluid sample is determined by repeatedly checking the current between the working and counting electrodes until a current is measured that is higher than a predetermined threshold, for example 250 nA. Next, at step 106, the glucose testing is completed by measuring currents from the electrodes at pre-defined times. At step 108, it is determined whether an "open" condition exists. The process for determining the "open" condition will be described with reference to FIG. 6c below. If an "open" condition is detected, then the process continues to step 112 and an error code is displayed. If an "open" condition is not detected, then the process ends.

Figure 6B:
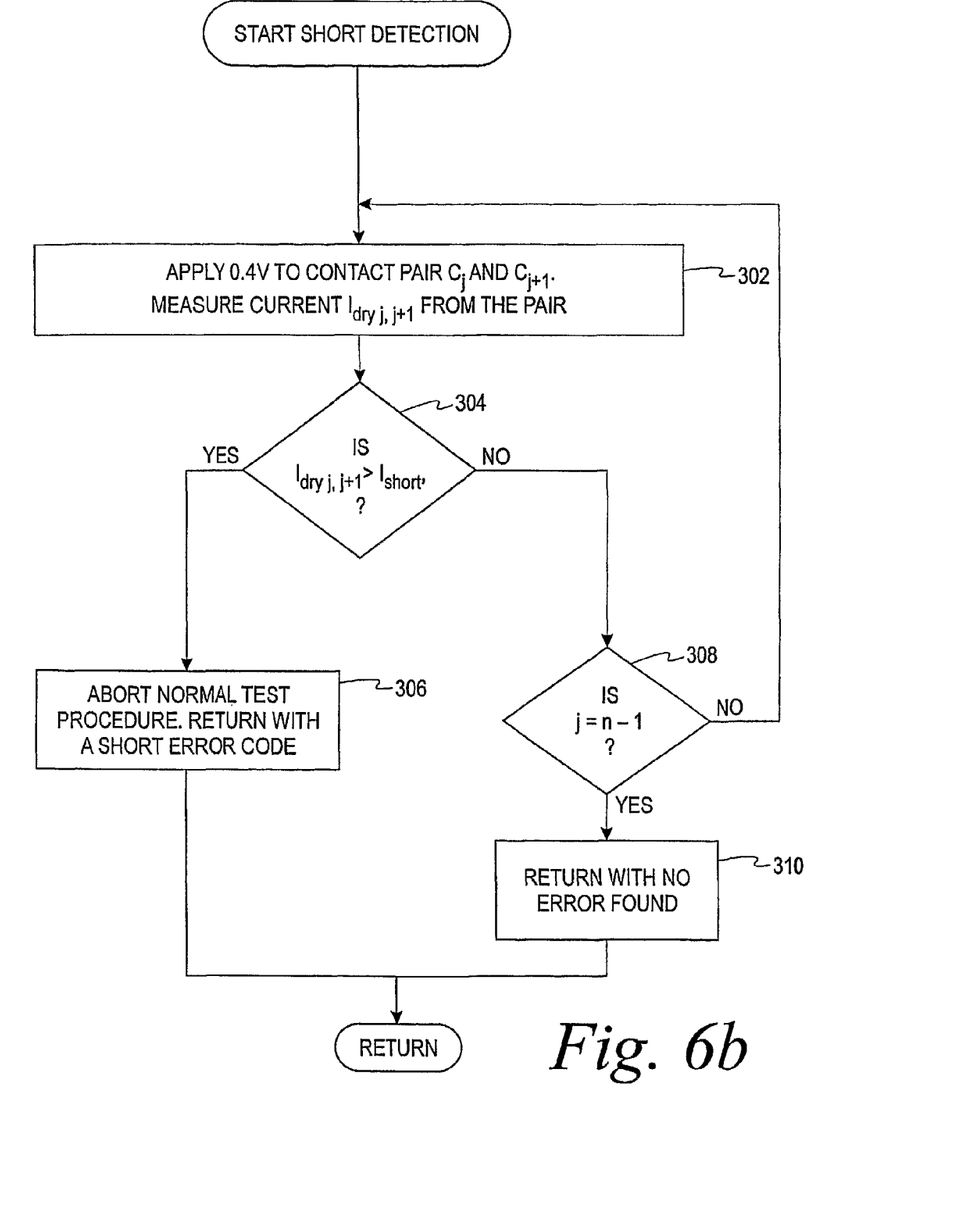

Turning now to FIG. 6b, a subroutine describing the process of determining whether a short exists will be described. As an initial matter, assume that $C_j$ and $C_{j+1}$ are neighboring contacts (j=1 to n−1) and that $I_{dry,j,j+1}$ is the current measured from the pair of contacts $C_j$ and $C_{j+1}$ before the sample has been introduced into the biosensor 10. At step 302, a voltage is applied to the contact pair $C_j$ and $C_{j+1}$. In this example, the voltage is between the range of about 0.2 to about 3.0 volts, preferably, about 0.4 volts. The current $I_{dry,j,j+1}$ is then measured from the pair. At step 304, the process determines whether the current $I_{dry,j,j+1}$ is greater than a predefined threshold $I_{short}$. In some embodiments, the predefined threshold $I_{short}$ is between about 20 nA to about 200 nA. If the current $I_{dry,j,j+1}$ is greater than the predefined threshold $I_{short}$, then the process continues to step 306 and the normal test procedure is aborted and an error code is supplied as described in FIG. 6a.

If the current $I_{dry,j,j+1}$ is not greater than a predefined threshold $I_{short}$, at step 308, the process determines whether j is equal to n−1? If no, the process returns to step 302, and performs the test for the next pair of neighboring connector contacts 42. If the answer is yes, then at step 310, the process returns a response of no error and continues with the main routine of FIG. 6a.

Figure 6C:
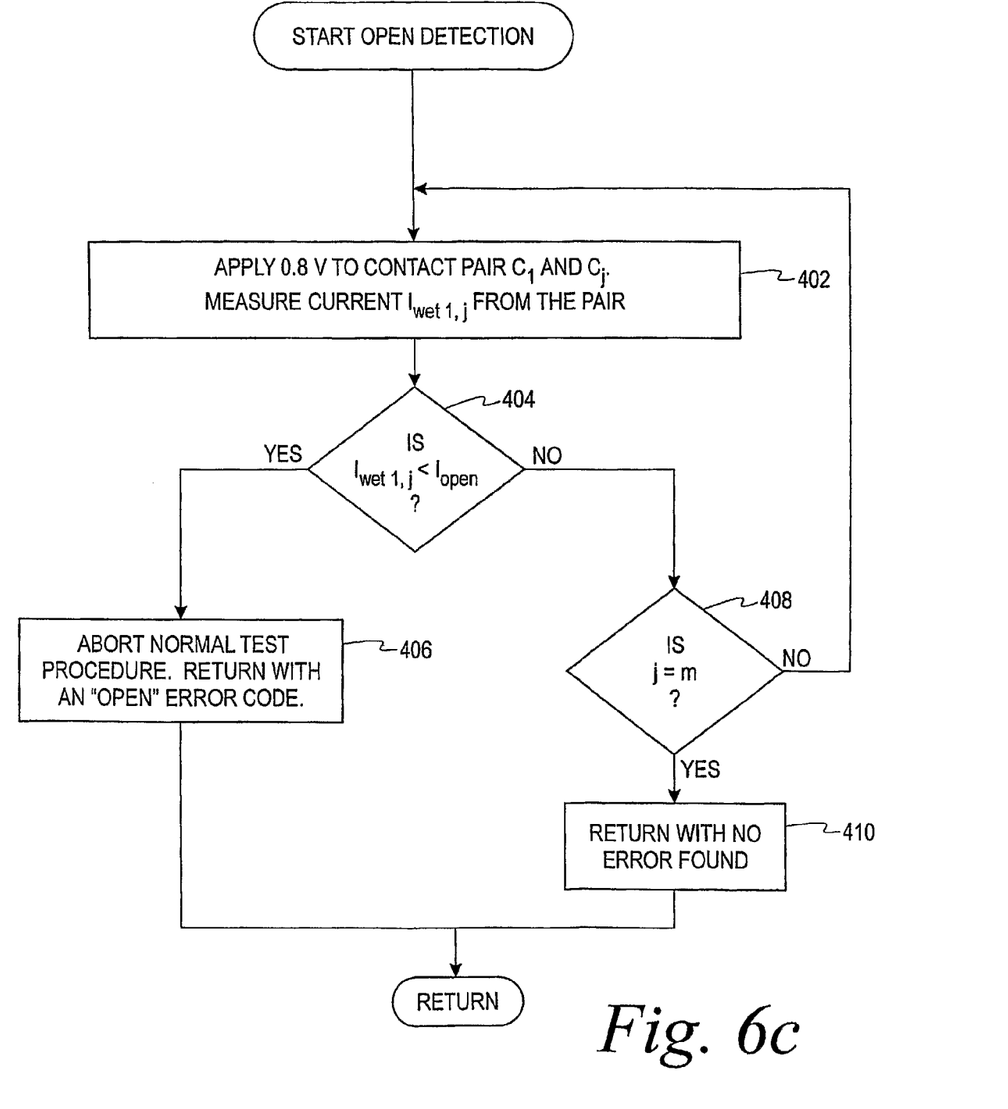

Turning now to FIG. 6c, a flow chart describing the subroutine of detecting an "open" contact error will be described. First, assume that j=2 to m, with m being the number of contacts in the connector. $C_1$ is a contact connected to the counter electrode of a sensor and is usually connected to 0 V in the meter. $C_1$ and $C_j$ are a pair of contacts. During the "open" testing, there are only m−1 pairs of contacts. $I_{wet1,j}$ is the current measured from the pair of contacts $C_1$ and $C_j$. As described above, the current $I_{wet1,j}$ is measured after the sample has been introduced into the biosensor 10. At step 402, a voltage is applied to the contact pair $C_1$ and $C_j$. The voltage should be in the range of about 0.2 to about 3.0 volts and preferably, should be about 0.8V. The current $I_{wet1,j}$ is measured between the pair of contacts $C_1$ and $C_j$. At step 404, it is determined whether the current $I_{wet1,j}$ is less than an open current $I_{open}$. The open current $I_{open}$ is a predefined threshold between about 20 to about 200 nA. If the measured current $I_{wet1,j}$ is less than a predefined threshold $I_{open}$, then the process continues to step 406, and the normal test procedure is aborted, and an "open" error code is displayed as discussed above in FIG. 6a.

If the measured current $I_{wet1,j}$ is not less than an open current $I_{open}$, then at step 408 the process determines whether j is equal to m. If j does not equal m, then the process returns to step 402, and tests the next pair of contacts. If j does equal m, then the process advances to step 410 and the subroutine ends without sending an error message.

Figure 7:
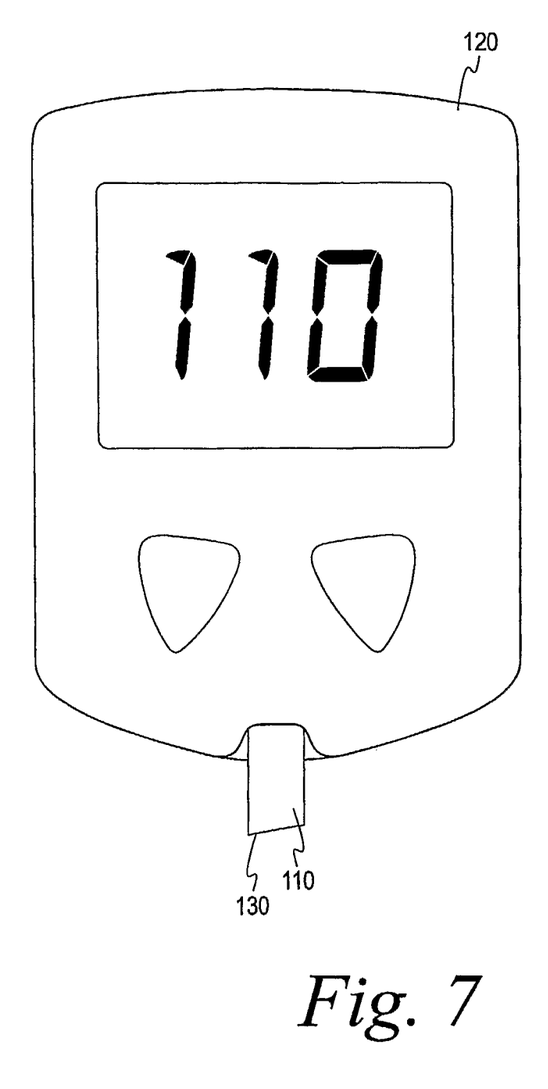
FIG. 7 is a top view of a meter using a single biosensor according to one embodiment of the present invention.

The above embodiments all relate to a test sensor system utilizing a cartridge. However, the present invention may also be used with a single sensor meter 120 as shown in FIG. 7. In FIG. 7, a user manually inserts one biosensor 110 is inserted into the meter 120 at a time. The biosensor 110 is inserted into the meter 120 such that a test end 130 sticks out of the meter 120 and the terminal end (not shown) is inserted into the meter. The biosensor 110 contains leads as described above, and the test meter 120 includes contacts that connect the leads. The testing of the connection between the connector contacts and the leads is as described above.

Also, although the present invention has been described using four leads, any number of leads may be used. In other embodiments, the meter may measure signals other than current between pairs of connector contacts.

Alternative Process A

A method of operating a meter for determining the concentration of an analyte in a current sample, the method comprising the acts of:
providing a biosensor and a meter;
providing a connector in the meter with a plurality of contacts;
coupling each of the plurality of contacts to one of a plurality of electrical leads on the biosensor, such that each of the plurality of connector contacts electrically contacts a corresponding one of the plurality of electrical leads;
obtaining a first measurement between at least one pair of the plurality of connector contacts via the meter prior to the fluid sample being applied;
obtaining a second measurement between at least one pair of the plurality of connector contacts via the meter after the fluid sample is applied; and
in response to one of the first and second measurements being outside of a predetermined range, the meter indicates a fault.

Alternative Process B

The method of Alternate Process A, wherein the first and second measurements obtained are current measurements.

Alternative Process C

The method of Alternate Process B, wherein in response to the first measurement prior to the sample being applied being greater than about 20 nA, the meter indicates a fault.

Alternative Process D

The method of Alternate Process B, wherein in response to the second measurement after the sample being applied being less than about 200 nA, the test device indicates a fault.

Alternative Process E

The method of Alternate Process A, further comprising applying a voltage to each pair, one pair at a time, of the plurality of connector contacts via the meter.

Alternative Process F

The method of Alternate Process A, wherein the voltage is from about 0.2 to about 3.0 volts.

Alternative Process G

The method of Alternate Process A, wherein the meter obtains a measurement between each pair, one at a time, of the plurality of connector contacts.

Alternative Process H

A method of operating a meter for determining the concentration of an analyte in a fluid sample, the method comprising the acts of:
positioning a biosensor into the testing position, the biosensor including a plurality of leads, the plurality of leads contacting one of a plurality of connector contacts in the meter;
obtaining a first current measurement between a pair of the of the plurality of connector contacts via the meter;
introducing a fluid sample into the meter;
obtaining a second current measurement between a pair of the plurality of connector contacts via the meter after the fluid sample is applied; and
in response to at least one of the first and second current measurements being outside a predetermined range, indicating a fault.

Alternative Embodiment I

A test system for determining the concentration of an analyte in a fluid sample, the system comprising:
a meter having a connector with a plurality of contacts; and
a biosensor having a plurality of leads, each of the plurality of leads adapted to contact a respective one of the plurality of contacts;
wherein the meter is further adapted to take a first measurement between a pair of the plurality of connector contacts prior to the fluid sample being applied and a second measurement after the fluid sample is applied, and, in response to one of the first and second measurements being outside a predetermined range, the meter is adapted to indicate a fault.

Alternative Embodiment J

The system of Alternate Embodiment I, wherein the measurement obtained is the current between the pair of the plurality of connector contacts.

Alternative Embodiment K

The system of Alternate Embodiment J, wherein in response to the measurement prior to the fluid sample being applied is greater than about 20 nA, the meter indicates a fault.

Alternative Embodiment L

The system of Alternate Embodiment J, wherein in response to the measurement after the fluid sample is applied is less than about 200 nA, the meter indicates a fault.

Alternative Embodiment M

The system of Alternate Embodiment I, wherein the meter is adapted to apply a voltage to each pair, one pair at a time, of the plurality of connector contacts, one pair at a time.

Alternative Embodiment N

The system of Alternate Embodiment M, wherein the voltage is between about 0.2 and 3.0 volts.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A method of operating a meter for determining the concentration of an analyte in a fluid sample, the method comprising the acts of:
   providing a biosensor and a meter;
   providing a connector in the meter with a plurality of connector contacts;
   positioning a biosensor in the meter, the biosensor including a plurality of leads, at least two of the plurality of leads being configured to contact at least one of the plurality of connector contacts in the meter;
   obtaining a first measurement between at least one pair of the plurality of connector contacts via the meter prior to the fluid sample being applied;
   determining if a short condition exists based on the first measurement;
   obtaining a second measurement between at least one pair of the plurality of connector contacts via the meter after the fluid sample is applied; and
   determining if an open condition exists based on the second measurement.

2. The method of claim 1, wherein the first and second measurements obtained are current measurements.

3. The method of claim 2, wherein a fault exists if the first measurement prior to the sample being applied is greater than about 20 nA.

4. The method of claim 2, wherein an open condition exists if the second measurement after the sample is applied being less than about 200 nA.

5. The method of claim 1, further comprising applying a voltage to each pair, one pair at a time, of the plurality of connector contacts via the meter.

6. The method of claim 5, wherein the voltage is from about 0.2 to about 3.0 volts.

7. The method of claim 1, wherein the meter obtains a measurement between each pair, one at a time, of the plurality of connector contacts.

8. A method of operating a meter for determining the concentration of an analyte in a fluid sample, the method comprising the acts of:
   positioning a biosensor in the test position, the biosensor including a plurality of leads, the plurality of leads contacting one of a plurality of connector contacts in the meter;
   obtaining a first current measurement between a pair of the of the plurality of connector contacts via the meter;
   after obtaining the first current measurement, introducing a fluid sample into the meter;
   obtaining a second current measurement between the pair of the plurality of connector contacts via the meter after the fluid sample is applied;
   in response to the first current measurements being outside a predetermined range, indicating a short condition fault; and
   in response to the second current measurements being outside a predetermined range, indicating an open condition fault.

9. A test system for determining the concentration of an analyte in a fluid sample, the system comprising:
   a meter having a connector with a plurality of contacts; and
   a biosensor having a plurality of leads, at least two of the plurality of leads being configured to contact at least two of the plurality of connector contacts;
   wherein the meter is configured to take a first measurement between a pair of the plurality of connector contacts prior to the fluid sample being applied and a second measurement after the fluid sample is applied, to determine if a short condition exists based on the first measurement, and to determine if an open condition exists based on the second measurement.

10. The system of claim 9, wherein the measurement obtained is the current between the pair of the plurality of connector contacts.

11. The system of claim 10, wherein a fault exists if the measurement prior to the fluid sample is applied is greater than about 20 nA.

12. The system of claim 10, wherein an open condition exists if the measurement after the fluid sample is applied is less than about 200 nA.

13. The system of claim 9, wherein the meter is adapted to apply a voltage to each pair, one pair at a time, of the plurality of connector contacts, one pair at a time.

14. The system of claim 13, wherein the voltage is between about 0.2 and 3.0 volts.

15. The method of claim 1, wherein the short condition exists when at least one of the plurality of connector contacts is in contact with two or more of the plurality of leads when the biosensor is positioned in the meter, and the open condition exists when at least one of the plurality of connector contacts is not in contact with any of the plurality of leads when the biosensor is positioned in the meter.

16. The method of claim 8, wherein the short condition fault is indicative of at least one of the plurality of connector contacts being in contact with two or more of the plurality of leads when the biosensor is positioned in the test position, and the open condition fault is indicative of at least one of the plurality of connector contacts being not in contact with any of the plurality of leads when the biosensor is positioned in the test position.

17. The test system of claim 9, wherein the short condition exists when at least one of the plurality of connector contacts is in contact with two or more of the plurality of leads, and the open condition exists when at least one of the plurality of connector contacts is not in contact with any of the plurality of leads.

18. A method of operating a meter for determining the concentration of an analyte in a fluid sample, the method comprising the acts of:

providing a biosensor and a meter;

providing a connector in the meter with a plurality of connector contacts;

positioning a biosensor in the meter, the biosensor including a plurality of leads, at least two of the plurality of leads being configured to contact at least a respective one of the plurality of connector contacts in the meter;

obtaining a first measurement between at least one pair of the plurality of connector contacts via the meter prior to the fluid sample being applied;

determining whether at least one of the plurality of connector contacts is in contact with two or more of the plurality of leads based on the first measurement obtained prior to the fluid sample being applied, the determining based on the first measurement prior to the fluid sample being applied including determining whether an open condition exists;

obtaining a second measurement between at least one pair of the plurality of connector contacts via the meter after the fluid sample is applied; and determining whether at least one of the plurality of connector contacts is not in contact with any of the plurality of leads based on the second measurement obtained after the fluid sample is applied, the determining based on the second measurement after the fluid sample is applied including determining whether a short condition exists.

19. The method of claim 15, further comprising indicating a fault if it is determined that at least one of the plurality of connector contacts is in contact with two or more of the plurality of leads or one of the plurality of connector contacts is not in contact with any of the plurality of the leads.

20. The test system of claim 17, wherein the meter is further adapted to indicate a fault if it is determined that at least one of the plurality of connector contacts is in contact with two or more of the plurality of leads or one of the plurality of connector contacts is not in contact with any of the plurality of the leads.

* * * * *

UNITED STATES PATENT AND TRADEMARK OFFICE
CERTIFICATE OF CORRECTION

| | | Page 1 of 1 |
|---|---|---|
| PATENT NO. | : 8,496,801 B2 | |
| APPLICATION NO. | : 11/988426 | |
| DATED | : July 30, 2013 | |
| INVENTOR(S) | : Huang | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 914 days.

Signed and Sealed this
Tenth Day of February, 2015

Michelle K. Lee
*Deputy Director of the United States Patent and Trademark Office*